US005702881A

United States Patent [19]
Brasile et al.

[11] Patent Number: 5,702,881
[45] Date of Patent: Dec. 30, 1997

[54] METHOD AND SOLUTION FOR ORGAN PRESERVATION COMPRISING RETINAL-DERIVED GROWTH FACTOR, CYCLODEXTRIN, MUCOPOLYSACCHARIDE AND FLUOROCARBON

[75] Inventors: Lauren Brasile, Albany; Jolene Clarke, Ballston Spa, both of N.Y.

[73] Assignee: Alliance Pharmaceutical Corp., San Diego, Calif.

[21] Appl. No.: 476,456

[22] Filed: Jun. 7, 1995

Related U.S. Application Data

[63] Continuation-in-part of Ser. No. 33,629, Mar. 16, 1993, abandoned.
[51] Int. Cl.$^6$ .................... A01N 1/02; C12N 5/00
[52] U.S. Cl. .................... 435/1.2; 435/1.1; 435/405; 435/407
[58] Field of Search .................. 435/1.2, 1.1, 1.3, 435/240.3, 240.31, 405, 407

[56] References Cited

U.S. PATENT DOCUMENTS

| Re. 34,077 | 9/1992 | Segall et al. | 604/52 |
|---|---|---|---|
| 3,975,512 | 8/1976 | Long | 424/5 |
| 4,289,499 | 9/1981 | Clark, Jr. et al. | 23/230 B |
| 4,920,044 | 4/1990 | Bretan, Jr. | 435/1 |
| 5,057,494 | 10/1991 | Sheffield | 514/12 |
| 5,077,036 | 12/1991 | Long, Jr. | 424/5 |
| 5,114,932 | 5/1992 | Runge | 514/58 |
| 5,356,771 | 10/1994 | O'Dell | 435/1 |
| 5,385,821 | 1/1995 | O'Dell | 435/1 |

FOREIGN PATENT DOCUMENTS

| 033402A1 | 1/1980 | European Pat. Off. |
| 9502326 | 1/1995 | WIPO |
| 9512310 | 5/1995 | WIPO |

OTHER PUBLICATIONS

Bonventre, et al. "Kidney Preservation Ex Vivo For Transplantation" Annu. Rev. Med. 43: 523–553 (1992).

Booster, et al. "In Situ Preservation of Kidneys From Non–Heart–Beating Donors: A Proposal for a Standardized Protocol" Transplantation 56(3):613–617 (1993).

Brasile, et al. "Postmortem Organ Salvage Using an Oxygen™ Supplemented Perfusate" Art. Cells. Blood Subs., and Immob. Biotech. 22(4): 1469–1475 (1994).

Hoshino, et al. "Ablation of Free Radical–Mediated Reperfusion Injury for the Salvage of Kidneys Taken from Non–Heartbeating Donors" Transplantation 45(2): 284–289 (1988).

"Organ Perfusion with Flurocarbon Fluid" Gollan, et al., *The Physiologist*, 9:191 (1966).

"Fluorocarbon Sonicated as a Substitute for Erythrocytes in Rat Liver Perfusion" Brown, et al., *Surgery*, 71: No. 3, pp. 388–394 (1972).

"A Perfluorochemical Oxygen Carrier (Fluosol–43) in a Synthetic Medium Used for Perfusion of Isolated Rat Liver" Novakova, et al., *Acta physiol. scand.*, 98:356–365 (Apr. 1976).

"The Evaluation of Synthetic Oxygen Carriers by Perfusion of Isolated Rat Liver" Novakova, *Acta physiol. scand.*, 98:433–439 (Apr. 1976).

"Organ Perfusion with Perfluorocarbon" Hall, et al., *Blood Substitutes and Plasma Expanders*, 41–56 (1978).

"Perfusion of the Brain and Other Isolated Organs with Dispersed Perfluoro Compounds" Sloviter, *Blood Substitutes and Plasma Expanders*, 27–39 (1978).

"Les fluorocarbones comme substitut sanguin" Faradji, et al., *Reveu Française de Transfusion et d'Immuno–hematslogio*, 22:119–133 (1979).

"Ex vivo Functional Evaluation of Pig Hearts Subjected to 24 hours' Preservation by Hypothermic Perfusion" Wicomb, et al., *SA Med. Journal*, 60:245–248 (Aug. 1, 1981).

"Generation of Plasmatic Coagulation Factors by Isolated Rat Liver Perfused with Completely Synthetic Blood Substitute" Owen, et al., *Thrombosis Research*, 22:259–266 (1981).

"Isolated Working Rat Heart Perfusion with Perfluorochemical Emulsion Fluosol–43" Segel, et al., *Am. J. Physiol.*, 242:H485–H489 (1982).

"Perfluorochemical Perfusion of the Rat Heart: In vivo and In vitro" Tomera, et al., *Journal of Molecular and Cellular Cardiology*, 14:573–585 (1982).

"Comparative $pO_2$ Histograms and Other Parameters in Canine Kidneys During Perfusion with Oxypherol" Ruland, et al., *Advances in Blood Substrates Researches*, 221–227 (1983).

"Development of a Perfluorochemical Emulsion as a Blood Gas Carrier" Mitsuno, et al., *Artif. Organs*, 8:25–33 (1984).

"Organ Preservation" Pegg. *Surgical Clinics of North America*, 66: No. 3, pp. 617–632 (Jun. 1986).

"Forty–Eight Hours Hypothermic Perfusion Storage of Pig and Baboon Hearts" Wicomb, et al., *Journal of Surgical Research*, 40:276–284 (1986).

"Twenty–Four–Hour Isolated Heart Preservation by Perfusion Method with Oxygenated Solution Containing Perfluorochemicals and Albumin" Kioka, et al., *Heart Transplant*, 5:437–443 (1986).

"Fluorocarbon preservation of kidney transplants" Chen, et al., *9–Biochem. Methods*, 106:339, cite 210441c (1987).

(List continued on next page.)

*Primary Examiner*—Sandra E. Saucier
*Attorney, Agent, or Firm*—Knobbe, Martens, Olson & Bear

[57] ABSTRACT

The present invention is directed to a new preservation solution useful for the initial flushing and for the storage of organs intended for transplantation using a warm preservation technology, between 18° C. and 37° C. Among the components of the preservation solution are a basal mammalian cell culture medium comprising one or more serum proteins, growth factors, particularly retinal-derived growth factor mucopolysaccharides, and emulsified liquid fluorocarbons, and cyclodextrin.

25 Claims, 2 Drawing Sheets

OTHER PUBLICATIONS

"The Effect of Fluorocarbon Emulsion on 24–hour Canine Heart Preservation by Coronary Perfusion" Gohra, et al., *Annals of Thoracic Surgery*, 48:96–103 (1989).

"Extended Ex Vivo Preservation of the Heart and Lungs: Effects of Acellular Oxygen–Carrying Perfusates and Indomethacin on the Autoperfused Working Heart–Lung Preparation" Kaplan, et al., *Thoracic Cardiovascular Surgery*, 100:687–698 (1990).

"Hep–Catabolism During 24 HR Cardiac Preservation Using 6 Different Solutions" Minten, et al., *The International Journal of Artificial Organs*, 13: No. 9, p. 604, cite 11.8 (1990).

"Maintien en Survie Extracorporelle et en Normothermie de Blocs Multivisèraux chex 1a Rat" Voglio, et al., *Chirugie*, 116:690–698 (1990).

"Enhanced Restoration of Adenine Nucleotides in Rat Liver Following Extended Preservation in UW Solution by Provision of Adenosine During Reperfusion" Palombo, et al., *Transplantation*, 51: No. 4, pp. 867–873 (Apr. 1991).

"Clinical Trial of University of Wisconsin Solution for Cardiac Transplantation: Preliminary Results" Drinkwater, *Journal of Thoriacic Cardiovascular Surgery*, 102:798–808 (1991).

"Energy Metabolism of Porcine Liver During a 72–hour Hypothermic Perfusion with UW Solution" Yamamoto, et al., *Eur Surg Res*, 23:27–34 (1991).

"Seventy–Two–Hour Preservation of Porcine Liver by Continuous Hypothermic Perfusion with UW Solution in Comparison with Simple Cold Storage" Yamamoto, et al., *Journal of Surgical Research*, 51:288–292 (1991).

"Use of an Artificial Oxygen Carrier in Isolated Rat Liver Perfusion: First Demonstration of Net Glucose Uptake . . . " Plauth, et al., *Research Experimental Medicine*, 191:339–347 (1991).

"Oxygenation of the Human Pancreas During Preservation by a Two–Layer Cold Storage Method" Kuroda, et al., *Transplantation*, 54: No. 3, pp. 561–562 (Sep. 1992).

"Fluorochemical Emulsion APE–LM Substantially Improves Cardiac Preservation" Segel, et al., *Am. J. Physiol.*, 263:H730–H739 (1992).

"Long–Term Preservation of Canine Pancreas by a New Simple Cold Storage Method Using Perfluorochemical—The Two–Layer Cold Storage Method (Euro–Collins Solution/Perfluorochemical)" Kawamura, *Kobe J. Med. Sci.*, 38:135–145 (1992).

Nakaya S et al., "Proceedings Xth Int. Cong. Nutrition: Symp. on Perfluorochemical Artificial Blood", Kyoto pp 187–201 (1975).

ns, 881

METHOD AND SOLUTION FOR ORGAN PRESERVATION COMPRISING RETINAL-DERIVED GROWTH FACTOR, CYCLODEXTRIN, MUCOPOLYSACCHARIDE AND FLUOROCARBON

RELATED APPLICATION

This application is a continuation-in-part application of U.S. patent application Ser. No. 08/033,629, filed Mar. 16, 1993, now abandoned.

FILED OF THE INVENTION

The present invention relates to a solution for use in preserving organs and tissues and a method for organ preservation. More specifically, the invention comprises a method for the preservation of organs without traditional hypothermia using a perfusate supplemented with an emulsified liquid fluorocarbon.

BACKGROUND OF THE INVENTION

In vitro organ preservation was originally described by Carrel and Lindberg in 1938. Since their original studies, many researchers have attempted to preserve organs prior to transplantation. Over the subsequent years, the longest experimental preservation times achieved have been approximately five to seven days for kidneys. This may be due to the fact that organ preservation studies embarked upon a path using hypothermic conditions very early on. In 1937, Bickford and Winton noted that hypothermia prolonged the duration of tissue survival since hypothermia reduces the metabolic need of an organ. At 25° C., there was a 25% reduction of blood flow in the kidney and the creatinine clearance was reduced by 20%. Below 18° C. hypothermia inhibits the tubular activity of the kidney. At 4° C., the use of oxygen is approximately 5% of that at normothermia.

A direct relationship exists between oxygen requirements and temperature. In fact, hypothermia may exert a greater depression of oxidative metabolism in the kidney than in the body as a whole and this may help to explain the success in preserving kidneys relative to other organs. A major portion of the oxygen consumed by the kidney is used for the process of active sodium reabsorption, and sodium reabsorption is by far the most important of all the tubular transport processes. Hypothermic storage, however, is not benign. It produces vasospasm and subsequent edema in an allograft. Preserved organs experience glomerular endothelial cell swelling and loss of vascular integrity along with tubular necrosis, which can be attributed to the hypothermia. Hypothermia inhibits Na/K dependent ATPase and results in the loss of the cell volume regulating capacity. The loss of volume regulation is what causes the cellular swelling and damage. An ample supply of oxygen actively diminishes the amount of this swelling. The most successful early organ preservation studies employed either supplementation with hemoglobin or a pump-lung system. Without adequate oxygen delivery, anoxia leads to disintegration of the smaller vessels after several hours of perfusion.

Accordingly, supplying adequate oxygen delivery to the organ has been a major obstacle to successful organ preservation. The inability to supply oxygen led to the current reliance on hypothermia. And yet, the hypothermia itself may represent the rate-limiting factor in organ preservation. The lack of oxygen and the subsequent depletion of ATP stores mean that anaerobic glycolysis is the principal source of energy under traditional preservation conditions. Therefore, glycolysis is the only source of ATP available to anoxic cells.

It is well known that hypothermic conditions eliminate the effective use of oxygen by tissues. At normal physiologic temperatures, the phospholipids making up the cell membranes are highly fluid. Under hypothermic conditions, the lipid bi-layer experiences a phase-change and becomes gel-like, with greatly reduced fluidity. The essentially frozen lipid in the cell membranes negates the use of oxygen, even in the presence of a high oxygen-tension. The metabolic consequence is glycolysis, which is analogous to the state of anoxia. The hypothermic conditions used in organ preservation probably represent the reason why previous studies in which the oxygen-tension was raised did not uniformly demonstrate the benefit of increased oxygenation of tissues.

It has been estimated that approximately one third of the energy metabolism of cells is expended to maintain the sodium pump and to preserve cell volume. The lack of molecular oxygen for oxidative phosphorylation which occurs in ischemia leads to the accumulation of NADH and the depletion of ATP stores within the mitochondria. The subsequent loss of nucleosides is probably a very important factor in the failure of tissues subjected to warm ischemia and prolonged periods of cold ischemia to regenerate ATP after restoration of the blood supply.

The development of warm preservation technology would present the opportunity to support near normal metabolic activity. In order to support the increased metabolic rate, an increased oxygen-tension will be required for respiration. Extending the period of organ preservation in vitro further cannot be achieved without increasing the metabolic activity suppressed by the hypothermia and in turn supplying adequate oxygen and metabolite delivery to support this basal metabolism.

Currently, kidney transplantation is largely dependent upon the availability of organs retrieved from heartbeating cadaver donors. While awaiting transplantation, kidneys must be stored in a fashion that will result in the restoration of normal, immediate function. Therefore, the clinical preservation of organs is much more limited than the experimental models; approximately 48 hours for kidneys, 18 hours for livers and 4–6 hours for hearts. There are two methods of storage for kidney—preservation by continuous hypothermic perfusion and simply hypothermic storage. While a variety of perfusates have been used clinically, these two methods of kidney storage have remained substantially unchanged for the past 25 years. VIASPAN, manufactured and marketed by DuPont, represents state-of-the-art organ preservation. VIASPAN, originally developed as the University of Wisconsin (UW) solution, provides for optimized organ preservation under hypothermic conditions. While VIASPAN minimizes the edema and vasospasm normally encountered during hypothermic storage, its use is limited to the current methods of hypothermic perfusion and storage. VIASPAN contains components which prevent hypothermic induced tissue edema, metabolites which facilitate organ function upon transplantation, anti-oxidants, membrane stabilizers, colloids, ions and salts.

The formulation of this perfusate is designed to preserve the kidney allografts by hypothermic induced depression of metabolism. The clinical preservation times have not been extended; it is not designed as a perfusate that provides an opportunity to expand the currently limited donor pool. This is due to the fact that an allograft marginally damaged by warm ischemia cannot tolerate further damage mediated by the hypothermia. Until a mechanism for organ preservation is developed which will provide for the use of an expanded donor pool, the severe shortage of organs in the U.S. cannot be met.

There is a need for the development of more efficient preservation technology. Better quality preservation will also provide the opportunity to expand the donor pool. Allografts with marginal function, secondary to warm ischemia, could theoretically be used because further damage via hypothermic preservation would be eliminated.

The current demand for organs cannot be met unless new sources of organs can be developed. And yet, the donor pool cannot be substantially expanded with existing technology because the rapid cooling of organs and the use of high potassium solutions eliminate the possibility of instituting any concordant, life-saving measures. A large and as yet untapped source of organs for transplantation are accident victims who succumb at the accident site and those who have short post-trauma survival times. These accident victims are not used as organ donors because of the ischemic damage. A period of warm ischemia greater than 60 minutes leads to the phenomenon of no-reflow, which is the failure of circulation to return to the organ. If a suitable means of organ preservation could be developed which minimizes, or to some extent repairs, the damage due to warm ischemia, the shortage of organs could be largely alleviated. The development of warm preservation technology would present the unique opportunity of supporting both organ-salvage and life-saving protocols simultaneously. As stated above, with traditional techniques, patient life-saving measures and organ saving measures are mutually exclusive. The development of warm preservation technology would present the possibility for in vivo flushing which would satisfy patient survival and organ salvage protocols. By conservative estimates, this untapped pool of organ donors could provide approximately 10 times the number of organs currently being harvested in the U.S. The number of patients being maintained on hemodialysis has almost doubled in the last six years. Therefore, there is tremendous pressure in the U.S. to open new avenues of procuring transplantable organs. This building public pressure being placed on the medical community is reflected by the recent attempts at xenografting and the discussions pertaining to the sale of organs.

There is therefore an urgent need for a preservation solution useful for initial organ flushing and as a perfusate for ex vivo preservation of organs for transplantation using a warm preservation technology. This technology will minimize, or to some extent repair, the damage caused by warm ischemia, and may support the organ near normal metabolic rate. A desirable feature of using such a solution is that organ preservation ex vivo may be extended further by increasing metabolic activity suppressed by hypothermia, and by supplying adequate oxygen and metabolite delivery to support this basal metabolism.

Fluorocarbons are fluorine substituted hydrocarbons that have been used in medical applications as imaging agents and as blood substitutes. U.S. Pat. No. 3,975,512 to Long discloses fluorocarbons, including brominated fluorocarbons, for use as a contrast enhancement medium in radiological imaging. Brominated fluorocarbons and other fluorocarbons are known to be safe, biocompatible substances when appropriately used in medical applications.

It is additionally known that oxygen, and gases in general, are highly soluble in some fluorocarbons. This characteristic has permitted investigators to develop emulsified fluorocarbons as blood substitutes.

Injectable fluorocarbon emulsions act as a solvent for oxygen. They dissolve oxygen at higher tensions and release this oxygen as the partial pressure decreases. Carbon dioxide is handled in a similar manner. Oxygenation of the fluorocarbon when used intravascularly occurs naturally through the lungs. For other applications, the fluorocarbon can be oxygenated prior to use.

Thus, fluorocarbons represent a safe, biocompatible source of oxygen which can support basal metabolism. There is a need for further development of fluorocarbon technology for medical applications.

SUMMARY OF THE INVENTION

The present invention is directed to a preservation solution useful for the initial flushing and storage of organs intended for transplantation, and a method of preservation technology and transplantation useful at temperatures between 18° C. and 37° C. In accordance with one aspect of the present invention, there is provided a method for preserving an organ prior to transplantation, comprising the steps of flushing an organ with a preservation solution, and thereafter storing said organ at a temperature between about 18° C. and about 37° C. for at least 15 minutes. The preservation solution comprises a mammalian cell culture medium comprising one or more serum proteins, growth factors, mucopolysaccharides, emulsified liquid fluorocarbons, and cyclodextrin. The fluorocarbon comprises between about 1% and 50% v/v of the preservation solution. The flushing step can be performed in situ or ex vivo or the flushing and storing can be performed while the organ remains in situ or ex vivo. The method of the present invention preferably comprises the additional step of continuously perfusing the organ with the preservation solution.

In accordance with another aspect of the present invention, there is provided a preservation solution which supports the preservation of organs without hypothermia, comprising a mammalian cell culture medium comprising one or more serum proteins, growth factors, mucopolysaccharides, emulsified liquid fluorocarbons, and cyclodextrin. The fluorocarbon comprises between about 1% and 50% v/v of the preservation solution. In a preferred embodiment, the mammalian cell culture medium further comprises magnesium, amino acids, glucose, and salts. In preferred embodiments, the serum protein is albumin, the growth factor is bovine-retinal derived growth factor, and the fluorocarbon is perfluorooctylbromide.

The preservation solution preferably comprises a solution having an osmolarity of from about 330 to about 600 mOsM, and more preferably from about 340 to about 450 mOsM. The fluorocarbon preferably comprises between about 5% to about 40% v/v of the preservation solution, and more preferably between about 15% to about 25% v/v. The fluorocarbon emulsion preferably has a particle size of less than 0.5 microns.

Another aspect of the present invention provides a method for organ transplantation, comprising the steps of identifying an organ to be transplanted, flushing the organ with a preservation solution, continuously perfusing the organ with the preservation solution at a temperature between about 18° C. and about 37° C. for at least 15 minutes, and thereafter transplanting the organ into a recipient. The preservation solution comprises a mammalian cell culture medium comprising one or more serum proteins, growth factors, mucopolysaccharides, emulsified liquid fluorocarbons, and cyclodextrin. The fluorocarbon comprises between about 1% and 50% v/v of the preservation solution, preferably between about 5% to about 40% v/v of the preservation solution, and more preferably between about 15% and about 25% v/v.

The flushing step is performed in situ or ex vivo. Preferably, both the flushing step and the perfusing step are performed while the organ remains in situ or ex vivo.

In a preferred embodiment, the mammalian cell culture medium further comprises magnesium, amino acids, glucose, one or more polysaccharides and salts. The preservation solution comprises a solution having an osmolarity of from about 330 to about 600 mOsM, preferably from about 340 to about 450 mOsM.

DETAILED DESCRIPTION OF THE INVENTION

The present invention is directed to a new hyperosmolar solution particularly useful as a preservation solution for initial organ flushing, and/or as a perfusate for storage of organs using a warm preservation technology (18°–37° C.) without the need for extreme hypothermia. "Hyperosmolar" is used herein to indicate that the composition has an increased osmotic concentration as compared to basal mammalian cell culture medium and normal body fluids. Thus, hyperosmolar is represented by >330 mOsM.

The preservation solution or perfusate of the present invention comprises a basal mammalian cell culture medium supplemented with an emulsified liquid fluorocarbon, wherein the fluorocarbon comprises between about 1% and about 50% v/v of the preservation medium. The preservation solution or perfusate additionally comprises components designed to support the nutritional and metabolic needs of the vascular endothelium within a graft at temperatures between about 18° C. and 37° C., thereby maintaining the integrity of the vasculature and subsequently the normal permeability of the organ. One preferred embodiment of the invention comprises a highly enriched mammalian cell culture medium, supplemented with one or more emulsified liquid fluorocarbons, growth factors, serum proteins, mucopolysaccharides, and cyclodextrin. Another preferred embodiment of the preservation solution additionally comprises magnesium, amino acids, salts, one or more polysaccharides, ions, and glucose. The perfusate of the present invention is able to preserve organs without concomitant extreme hypothermia.

While the studies described herein relate to the preservation of renal allografts, the application of the preservation solution using a warm preservation technique relates to the preservation of other organs as well. The solution of the present invention was specifically designed to potentiate the simultaneous growth of microvessel and large vessel endothelial cells, to support the integrity of the vascular endothelium within a graft, and to support more normal permeability and metabolism without the need for extreme hypothermic conditions.

The preservation solution of the present invention advantageously employs a mammalian cell culture basal medium and one or more emulsified liquid fluorocarbons, to which is added a variety of supplements including one or more serum proteins such as transferrin, albumin and insulin, one or more growth factors, one or more mucopolysaccharides such as heparin and chondroitin sulfate, magnesium, cyclodextrin, pyruvate, amino acids, salts, one or more polysaccharides, ions and glucose. These supplements serve to enhance the ability of the solution of the present invention to serve as a preservation solution for organs for transplantation using a warm preservation technology. For example, serum albumin acts as a source of protein and colloid; glucose provides for metabolic support; cyclodextrin serves as a source of impermeant, a scavenger, and a potentiator of cell attachment factors; a very high $Mg^{++}$ concentration provides for microvessel metabolism support; mucopolysaccharides, comprising primarily chondroitin and heparin sulfates, provide growth factor potentiation and hemostasis; and an emulsified liquid fluorocarbon supplies the necessary oxygen. The perfusate is preferably hyperosmolar, with a final osmolarity after perfluorochemical emulsion supplementation of 330–600 mOsM, preferably from about 340–450 mOsM and more preferably about 350 mOsM.

The preservation solution of the present invention has been found to preserve organs without the need for extreme hypothermia, and also reduce or eliminate the common problems encountered with cold storage perfusates, namely edema, vasospasm, depletion of ATP stores, inhibition of ion pumps, glycolysis, and the generation of toxic free radical intermediates following reperfusion. The preservation solution of the present invention provides for more efficacious preservation thereby presenting the potential to use nonheartbeating cadaver donors, thus expanding the potential donor pool.

In addition, the present invention has direct applications for the preservation of the vasculature in any form of trauma, including infarction or aneurysm, involving ischemia or hemorrhage. Likewise, localized preservation of isolated anatomy is possible. The preservation solution and method of use of the present invention can also be used in cases of controlled ischemia during surgical procedures, as well as in the areas of limb salvage and organ repair.

Cell culture media suitable for use in the present invention include any basal mammalian cell culture media well known to those of skill in the art, including Dulbecco's Modified Eagle's medium, Ham's F-12 medium, Eagle's minimal essential medium, Medium 199, and the like, which is supplemented with the necessary components. These components include one or more serum proteins, growth factors, mucopolysaccharides, and cyclodextrin. At least one emulsified liquid fluorocarbon is then added to this supplemented basal medium to a final volume of between about 1% and 50% v/v to produce a solution useful in preserving organs for transplantation using warm preservation technology.

An exemplary formula of a preservation solution in accordance with the present invention is set forth below in Table I.

TABLE I

COMPOSITION OF THE BASAL PRESERVATION SOLUTION OF THE PRESENT INVENTION

| | Basal Medium Ranges | Formulation 1 |
|---|---|---|
| DL-Alanine | .001–5 g/L | .12 g/L |
| L-Arginine HCl | .001–5 g/L | .14 g/L |
| DL-Aspartic Acid | .001–5 g/L | .12 g/L |
| L-Cysteine HCL.H$_2$O | .0001–1 g/L | .00022 g/L |
| L-Cystine 2HCl | .001–5 g/L | .052 g/L |
| DL-Glutamic Acid | .001–5 g/L | .2672 g/L |
| L-Glutamine | .001–5 g/L | .2 g/L |
| Glycine | .001–5 g/L | .1 g/L |
| L-Histidine HCl.H$_2$O | .001–5 g/L | .04376 g/L |
| L-Hydroxyproline | .001–5 g/L | .02 g/L |
| DL-Isoleucine | .001–5 g/L | .08 g/L |
| DL-Leucine | .01–5 g/L | .24 g/L |
| L-Lysine HCl | .001–5 g/L | .14 g/L |
| DL-Methionine | .001–5 g/L | .06 g/L |
| DL-Phenylalanine | .001–5 g/L | .10 g/L |
| L-Proline | .001–5 g/L | .08 g/L |
| DL-Serine | .001–5 g/L | .10 g/L |
| DL-Threonine | .001–5 g/L | .12 g/L |
| DL-Tryptophan | .001–5 g/L | .04 g/L |
| L-Tyrosine.2Na | .001–5 g/L | .11532 g/L |
| DL-Valine | .001–5 g/L | .10 g/L |
| Adenine Hemisulfate | .001–5 g/L | .02 g/L |
| Adenosine Triphosphate.2Na | .0001–1 g/L | .002 g/L |
| Adenylic Acid | .00001–1 g/L | .0004 g/L |
| Alpha Tocopherol Phosphate.2Na | .000001–1 g/L | .00002 g/L |
| Ascorbic Acid | .000001–1 g/L | .0001 g/L |
| D-Biotin | .000001–1 g/L | .00002 g/L |
| Calciferol | .00001–1 g/L | .0002 g/L |
| Cholesterol | .00001–1 g/L | .0024 g/L |
| Choline Chloride | .00001–1 g/L | .001 g/L |
| Deoxyribose | .00001–1 g/L | .001 g/L |
| Folic Acid | .000001–1 g/L | .0002 g/L |
| Glutathione (Reduced) | .000001–1 g/L | .0001 g/L |
| Guanine HCl | .00001–1 g/L | .0006 g/L |
| Hypoxanthine | .00001–1 g/L | .0006 g/L |
| Menadione (Na Bisulfite) | .000001–1 g/L | .00003 g/L |
| Myo-Inositol | .000001–1 g/L | .0001 g/L |
| Niacinamide | .000001–1 g/L | .00005 g/L |
| Nicotinic Acid | .000001–1 g/L | .00005 g/L |
| PABA | .000001–1 g/L | .0001 g/L |
| D-Pantothenic Acid Ca | .000001–1 g/L | .00002 g/L |
| Polyoxyethylene-sorbitan Monooleate | .001–1 g/L | .04 g/L |
| Pyridoxal HCl | .000001–1 g/L | .00005 g/L |
| Pyridoxine HCl | .000001–1 g/L | .00005 g/L |
| Retinol Acetate | .00001–1 g/L | .00028 g/L |
| Riboflavin | .000001–1 g/L | .00002 g/L |
| Ribose | .00001–1 g/L | .001 g/L |
| Thiamine HCl | .000001–1 g/L | .00002 g/L |
| Thymine | .00001–1 g/L | .0006 g/L |
| Uracil | .00001–1 g/L | .0006 g/L |
| Xanthine.Na | .00001–1 g/L | .00069 g/L |
| Calcium chloride.2H$_2$O | .01–5 g/L | .265 g/L |
| Ferric Nitrate.9H$_2$O | .00001–1 g/L | .00144 g/L |
| Magnesium sulfate (anhydrous) | .001–5 g/L | 1.2 g/L |
| Potassium chloride | .01–5 g/L | .40 g/L |
| Sodium Acetate (anhydrous) | .001–5 g/L | .1 g/L |
| Sodium Chloride | 1–20 g/L | 6.8 g/L |
| Sodium Phosphate Monobasic (anhydrous) | .01–5 g/L | .244 g/L |
| Glucose | .1–5 g/L | 2.0 g/L |
| Insulin | .001–5 g/L | .01 g/L |
| Bovine serum albumin (BSA) | 1–100 g/L | 30 g/L |
| NaHCO$_3$ | 1–20 g/L | 4.4 g/L |
| Pyruvate | .01–5 g/L | .22 g/L |
| Transferrin | .001–5 g/L | .1 g/L |

TABLE I-continued

COMPOSITION OF THE BASAL PRESERVATION SOLUTION OF THE PRESENT INVENTION

| | Basal Medium Ranges | Formulation 1 |
|---|---|---|
| Fetal bovine serum (FBS) | 1–100 ml | 10 ml |
| Impermeant (Cyclodextrin) | .01–5 g/L | .5 g/L |
| Mucopolysaccharide (chondroitin sulfate B.) | .0001–1 g/L | .004 g/L |
| ENDO GRO | .001–5 g/L | .02 g/L |
| heparin | .01–5 g/L | .18 g/L |

ENDO GRO is a bovine retinal-derived growth factor which is effective in promoting cell proliferation with low serum concentration, and is available from VEC TEC, Inc., Schenectady, N.Y. It is an anionic heparin binding glycoprotein with a molecular weight of 18,000 and an isoelectric point of 4.5.

While it is contemplated that the various components of the basal cell culture medium set forth above may be mixed in a liter of distilled water to produce the formulation, there may exist various commercial preparations that contain many of the components, in the desired constituent ranges, of the basal medium, and that those components deficient in the particular commercial preparation can be added to that preparation to produce the basal formulation described above.

In addition to a basal cell culture medium, the preservation solution of the present invention also includes one or more emulsified liquid fluorocarbons. This fluorocarbon emulsion comprises from approximately 1% to 50% of the preservation solution (v/v). More preferably, the emulsified fluorocarbon comprises from about 5% to about 40% of the total solution (v/v), and even more prefereably from about 15% to about 25% (v/v). Fluorocarbon compounds useful in this invention are generally able to promote gas exchange, and most of these fluorocarbons readily dissolve oxygen and carbon dioxide. As is known in the art, emulsions having a particle size significantly greater than 0.4 microns tend to occlude small vessels and to collect too rapidly in the liver, spleen and other organs, enlarging them and endangering their function. Thus, the fluorocarbon emulsion of the present invention preferably has a particle size of less than about 0.5 microns.

There are a number of fluorocarbons that are contemplated for medical use. These fluorocarbons include bis(F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E"), cyclic fluorocarbons, such as C10F18 ("F-decalin," "perfluorodecalin" or "FDC"), F-adamantane ("FA"), F-methyladamantane ("FMA"), F-1,3-dimethyladamantane ("FDMA"), F-di-or F-trimethylbicyclo[3,3,1]nonane ("nonane"); perfluorinated amines, such as F-tripropylamine ("FTPA") and F-tributylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101").

Other fluorocarbons include brominated perfluorocarbons, such as 1-bromo-heptadecafluoro-octane ($C_8F_{17}Br$, sometimes designated perfluorooctylbromide or "PFOB"), 1-bromopentadecafluoroheptane ($C_7F_{15}Br$), and 1-bromotridecafluorohexane ($C_6F_{13}Br$, sometimes known as perfluorohexylbromide or "PFHB"). Other brominated fluorocarbons and fluorocarbon emulsions suitable for use in the present invention can be of the type described in U.S. Pat. No. 3,975,512 to Long, which also describes methods of preparing fluorocarbon emulsions. Also contemplated are fluorocarbons having nonfluorine substituents, such as perfluorooctyl chloride, perfluorooctyl hydride, and similar compounds having different numbers of carbon atoms.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}C_{n'}F_{2n'+1}$, $C_nF_{2n+1}OC_{n'}F_{2n'+1}$, or $C_nF_{2n+1}CF=CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed here, but having those properties described in this disclosure are additionally contemplated.

Preparation of fluorocarbon emulsions is well known and is described, for example, in U.S. Pat. No. 5,080,885. Such an emulsion was formerly sold by Alpha Therapeutics (Boston, Mass.) under the trademark FLUOSOL and is being developed by Alliance Pharmaceutical Corp. (San Diego, Calif.) under the trademark OXYGENT.

Particularly preferred fluorocarbon compounds for use in the present invention are the bromineted perfluorocarbons. Perfluorooctylbromide, or PFOB, is particularly preferred.

An emulsified liquid fluorocarbon is added to the supplemented cell culture medium to produce the preservation solution of the present invention. Such an emulsion can be prepared using the following components: PFOB, egg yolk phospholipid (EYP), $NaH_2PO_4$, $Na_2HPO_4$, $CaNa_2EDTA$, d-α Tocopherol, and NaCl. A particularly preferred formulation for a fluorocarbon emulsion is set forth in Table II below.

TABLE II

| Component | % w/v |
|---|---|
| PFOB | 90.0 |
| EYP | 4.0 |
| $NaH_2PO_4$ | 0.052 |
| $Na_2HPO_4$ | 0.355 |
| $CaNa_2EDTA$ | 0.02 |
| d-α Tocopherol | 0.002 |
| NaCl | 0.30 |

Another particularly preferred embodiment of the fluorocarbon emulsion of the present invention is set forth in Table III.

TABLE III perfluorocarbon: about 20–100% w/v
egg yolk phospholipid: about 2–10% w/v
sodium phosphate buffer: about 0.25–1.5% w/v
particle size: median range of 0.1–0.5 micron
pH: 6–7.5

The following examples further illustrate the use of the liquid fluorocarbon emulsion preservation solution of the present invention as a perfusate for organ preservation using a warm preservation technology. As used herein, "flush" describes the initial administration to or rinsing of an organ using the solution to remove existing blood from the blood vessels. By "perfusion" is meant the continuous administration of perfusate to the organ. Although the examples described herein disclose the use of a perfluorooctylbromide (PFOB) emulsion, the preferred fluorocarbon emulsion, other oxygen carrying fluorocarbons in an emulsified form may be used as well.

IN VITRO STUDIES

The following studies were performed to evaluate the efficacy of the perfusate of the present invention in preserving organs when compared with existing preservation methods and perfusate without perfluorochemical.

EXAMPLE 1

Pulsatile Preservation Characteristics

Canine kidneys were dissected using a midline incision. The renal arteries were identified and the kidneys were isolated with the vasculature intact. The renal arteries were then cannulated. After cannulation, the renal arteries were flushed with approximately 250 cc of the perfusate described in Formula 1, Table I. One set of kidneys was flushed with perfusate supplemented with 20% PFOB v/v (as a 90% emulsion) and another set was flushed with perfusate containing no PFOB. After flushing, the kidneys were placed on a modified Waters MOX-100 preservation system and pumped at 25° C. and 32° C. for up to 18 hours. A pulse rate of 60/minute was maintained with systolic pressures below 70 mmHg. A control set of kidneys were preserved using VIASPAN at 4° C., which represent state-of-the-art organ preservation.

Results a. Flow Characteristics

Mean pressures, pH and vascular flow rate data are listed below in Table IV:

TABLE IV

| | pressure (mm/Hg) | flow rate | pH |
|---|---|---|---|
| 25° C. | 50/30 | 75–120 cc/min | 7.35 ± 0.03 |
| 32° C. | 50/30 | 80–150 cc/min | 7.35 ± 0.05 |
| without PFOB at 25° C. | 50/30 | 75–120 cc/min | 7.25 ± 0.01 | b. Physical Appearance

The kidneys preserved with perfusate containing 20% PFOB experienced negligible weight gain during the period of preservation. The kidneys maintained normal turgor and displayed no discoloration. Kidneys preserved in either VIASPAN at 4° C. or in the perfusate without perfluorochemical supplementation experienced discoloration over time and had a net weight gain of approximately 20% and 10%, respectively.

c. Histology

Blinded histological studies revealed that all the kidneys were well preserved. There was no detectable difference between the kidneys preserved in perfusate with PFOB supplementation and those kidneys maintained in perfusate without the PFOB. The histologic evaluations revealed normal glomeruli and tubules. The control kidneys preserved with VIASPAN displayed normal glomeruli with focal dilated tubules along with focal edema.

d. Conclusion

The perfusate of the present invention provides for stable organ perfusion which does not alter over time. Factors such as pH, mean pressures and vascular flow rate can be maintained throughout the preservation period at both 25° C. and 32° C. Overall flow dynamics during preservation were quite similar in kidneys perfused with perfusate with or without PFOB supplementation. Kidneys preserved without PFOB supplementation, however, discolored over time and increased in weight. Similar discoloration and weight gain were seen in kidneys preserved with VIASPAN; these kidneys exhibited tubule damage as well. Accordingly, preservation using the perfusate of the present invention provides significant advantages over the state-of-the-art organ preservation.

EXAMPLE 2

Metabolism During Preservation

To determine the metabolism of the kidney during pulsatile preservation which is supported by the perfusate of the present invention, the following studies were performed.

Canine kidneys were dissected using a midline incision. The renal arteries were identified and the kidneys were then isolated with the vasculature intact. The renal arteries were then cannulated. After cannulation, the renal arteries were flushed with approximately 250 cc of the perfusate described in Formula 1, Table I, supplemented with 20% PFOB v/v (as a 90% emulsion). After flushing, the kidneys were placed on a modified Waters MOX-100 preservation system and preserved for 6 hours at 25° C. and 32° C. at a systolic pressure of approximately 50 mmHg. Blood gas specimens were collected at regular intervals in glass syringes. Samplings at each time point included the arterial feed line along the venous outflow. All testing was performed in duplicate. The $PO_2$ values were determined using an ABL 300 radiometer by Copenhagen.

To determine the effect of temperature during ex vivo organ preservation, 50 bovine kidneys were preserved ex vivo for six hours at 25° C. and 50 bovine kidneys were preserved ex vivo for six hours at 32° C. using the procedure described above. The kidneys were perfused with the preservation solution of the present invention as set forth in Formula 1 of Table I, supplemented with 20% PFOB v/v (as a 90% emulsion), with a modified pulsatile pump. Following 6 hours of ex vivo preservation, the metabolic function of the kidneys was evaluated. Glucose determinations were performed using a GEMSTAR II automated chemistry analyzer.

The results of the testing described above are listed below in Table V.

TABLE V

Metabolic Function After 6 hours Ex Vivo Preservation*

| | Perfusate 25° C. | Perfusate 32° C. | Perfusate w/o PFOB 25° C. |
|---|---|---|---|
| $O_2$ Consumed+ | 4.8 ml/min | 5.7 ml/min | <2.0 ml/min |
| Diuresis | 143.1 cc/hr | 123.3 cc/hr | 57.5 cc/hr |
| Histology | Normal | Normal | Normal |
| Glucose conc. @ | 72 mg/dL | *** | 105 mg/dL |

* - specimens collected after 6 hours of perfusion; values given represent the mean from experimental data in each group
+ - calculated using the method of Fick
@ - starting glucose concentration; 165 mg/dl
*** - below the threshold of sensitivity Kidneys preserved with the perfusate of this invention at either 25° C. or 32° C. demonstrated oxygen consumption rates greater than 4.0 mL/min. When the kidneys are preserved by pulsatile preservation at 25° C. in the basal perfusate without PFOB supplementation, however, the oxygen consumption rates were, in every case, less than 2.0 mL/min. The effect of this inadequate oxygen delivery, resulting in the low consumption rates, was that kidneys preserved without PFOB supplementation have a diminished diuresis.

These data demonstrate that the perfusate of the present invention supports a level of metabolism at either 25° C. or 32° C. which results in rates of oxygen consumption and diuresis approaching those of normal physiologic ranges.

EXAMPLE 3

Comparison of Ex Vivo Preservation Using Various Solutions

To determine the efficacy of the preservation solution of the present invention compared with various other solutions, the following experiments were performed. Using the procedure described above, the kidneys were dissected, the renal arteries were identified and the kidneys were isolated with the vasculature intact. The renal arteries were then cannulated. One hundred bovine kidneys and 30 canine kidneys were preserved ex vivo for six hours at 25° C.–32° C. by perfusion with the preservation solution of the present invention as set forth in Formula 1 of Table I, supplemented with 20% PFOB v/v (as a 90% emulsion), with a modified pulsatile pump. For comparison, 5 bovine kidneys were preserved ex vivo for six hours at 25° C.–32° C. by perfusion with a mammalian tissue culture medium, Medium 199, and 2 bovine kidneys were preserved ex vivo for six hours at 25° C.–32° C. by perfusion with Ringer's Lactate. Finally, 10 bovine and 5 canine kidneys were preserved ex vivo for six hours at 4° C.–8° C. by perfusion with VIASPAN. Following the period of preservation in the various solutions, the kidneys were tested for renal perfusion characteristics. The results of this testing are listed below in Table VI.

TABLE VI

Renal Perfusion Characteristics of Various Solutions

| | Mean mm Hg | Flow Rate (cc/min) | Diuresis (cc/hour) |
|---|---|---|---|
| Perfusate @ 25° C. | 30–50 | 75–150 | 60–150 |
| Medium 199 @ 25° C. | 60–100 | 60–100 | none |
| Ringer's @ 25° C. | 80–140 | 30–60 | none |
| VIASPAN @ 4° C. | 30–60 | 80–130 | none |

The data in Table VI demonstrate the superior performance of the preservation solution of the present invention in supporting the preservation of kidneys at near physiologic temperature (25° C.–32° C.) when compared with preservation using tissue culture media or Ringer's Lactate at 25° C., and VIASPAN at 4° C.

EXAMPLE 4

Long Term Preservation

Long term preservation at elevated temperatures has not previously been successful. Long term preservation at 25° C., however, is feasible with the perfusate of the present invention. Four kidneys were preserved by pulsatile preservation at 25° C. in the perfusate of the present invention according to the method described above. Table VII below demonstrates that stable preservation parameters can be maintained for time periods of at least 18 hours.

TABLE VII

| Long Term Preservation+ | | | |
|---|---|---|---|
| preservation time (hours) | perfusion pressure mm Hg | vascular flow rate cc/min | histology* |
| 3 | 50/30 | >80 | |
| 5 | 50/30 | >80 | |
| 8 | 50/30 | >80 | |
| 10 | 50/30 | >80 | |
| 12 | 50/30 | >80 | |
| 18 | 50/30 | >80 | Normal |

+ - represented as the mean of the data from four separate experiments at 25° C.
* - blinded histologic evaluations These results demonstrate that perfusion pressure and the resulting flow rates remain stable over time. The results of the blinded histologic evaluations indicated normal glomeruli and tubule structure following long term preservation with the perfusate of this invention at elevated temperatures.

TRANSPLANTATION STUDIES

The following experiments were performed to evaluate the efficacy of the perfusate of the present invention in preserving organs prior to transplantation, and the function of the preserved organs following transplantation.

EXAMPLE 5

Ex Vivo Preservation

Ex vivo preservation was performed using a canine autotransplantation model. The left kidney in six dogs was nephrectomized. The renal artery was cannulated and the kidneys were preserved ex vivo for six hours at 25° C. by perfusion with the preservation solution of the present invention as set forth in Formula 1 of Table I supplemented with 20% PFOB v/v (as a 90% emulsion), with a modified pulsatile pump. Following the period of ex vivo preservation in the perfusate, the kidneys were autotransplanted using an end-to-side anastomosis of the renal artery to the aorta and renal vein to the vena cava. During the reimplantation, a period of warm ischemia of approximately 35 minutes occurred. At the time of the autotransplantation, the contralateral, untreated kidney was nephrectomized so that the animal would be dependent upon the test kidney preserved in the perfusate.

Figure 1:
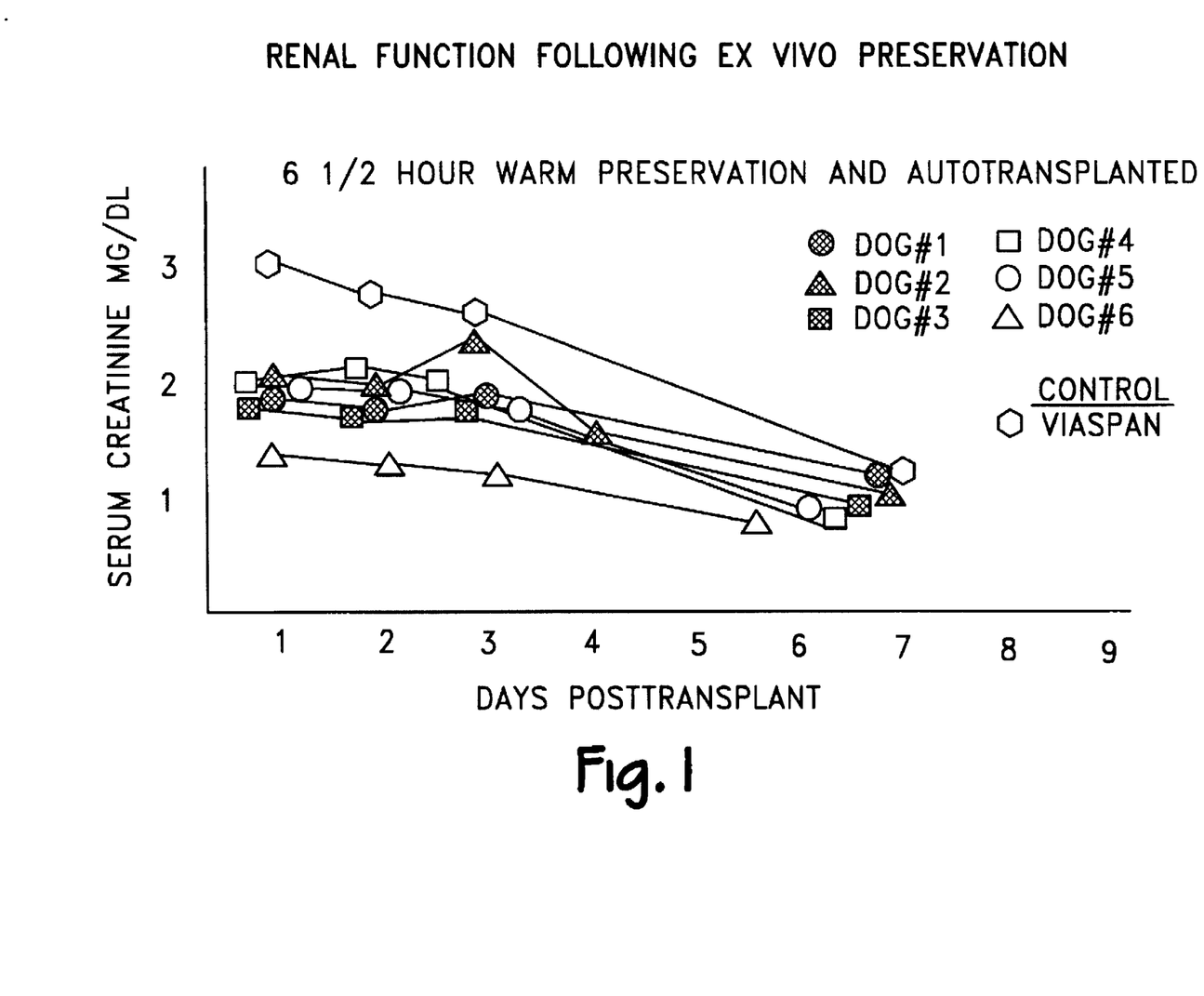
FIG. 1 graphically depicts renal function following ex vivo preservation with the preservation solution of the present invention and compares the results with those of a control without the preservation solution.

FIG. 1 illustrates the results of this testing. Normal renal function was seen in all six test animals where the autologous kidneys were preserved in the perfusate of the present invention for six hours at 25° C., with an additional period of 35 minutes of warm ischemia during reanastomosis.

In every case, the serum creatinine values at 24 hours posttransplant were less than 2.0 mg/dL. Similarly, all test kidneys produced urine within minutes of reperfusion, and the kidneys continued diuresis throughout the posttransplant period.

The control experiment consisted of a kidney preserved for six hours at 4° C. in VIASPAN. The control kidney was autotransplanted via the same technique described above. However, the kidney was kept at 4°–8° C. during the period of reanastomosis. This control animal demonstrated an elevated serum creatinine 24 hours posttransplant, which fell to within normal range by day three posttransplant (see FIG. 1). Therefore, the perfusate of the present invention provided superior preservation of the renal grafts when compared to that achieved with a state-of-the-art perfusate.

At the time of euthanasia, blinded histologic evaluations of the kidneys indicated that all kidneys were normal.

Thus, we have shown that the perfusate of the present invention can be used to preserve organs ex vivo at near physiologic temperatures. This preservation leads to immediate organ function with serum chemistries within the normal range.

EXAMPLE 6

In Situ Preservation

Two approaches were used to establish the efficacy of in situ preservation of canine kidneys using the perfusate of the present invention as set forth in Formula 1 of Table I, supplemented with 20% PFOB v/v (as a 90% emulsion). In the first, an autotransplant model, the renal vasculature was isolated by placing vascular clamps on the aorta and vena cava above and below the renal blood vessels. A cannula was placed in the aorta and vena cava through which the perfusate was perfused and recirculated in the kidneys at 37° C., after the autologous blood had been flushed. After three hours of in situ perfusion, the cannulas were removed and the aorta and vena cava were unclamped.

Figure 2:
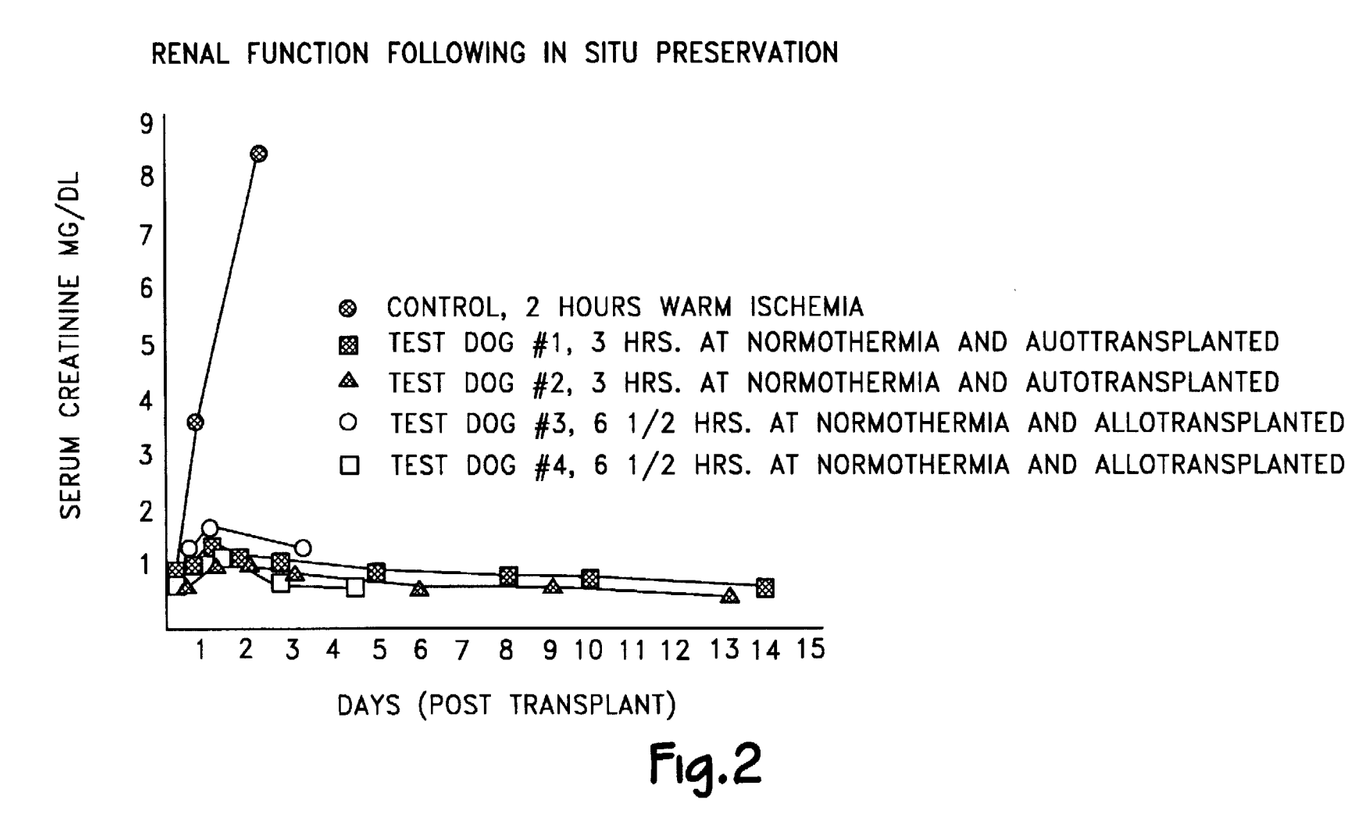
FIG. 2 graphically depicts renal function following in situ preservation with the preservation solution of the present invention and compares the results with those of a control without the preservation solution.

Reperfusion of the kidneys was immediate, without any signs of vasospasm or reperfusion injury. The kidneys functioned normally without any signs of renal damage. As depicted in FIG. 2, test dogs #1 and #2 showed normal renal function as measured by serum creatinine levels up to 13 and 14 days post transplant.

The second approach, an allotransplant model, entailed in situ preservation following euthanasia, similar to the in situ preservation technique described above. Following a six hour period of in situ preservation, the left kidney was nephrectomized and allotransplanted into a recipient dog. The kidney was allotransplanted with an end-to-side anastomosis of the renal artery to the aorta and renal vein to the vena cava. The two native kidneys were nephrectomized at the time of the allotransplantation so that each animal would be dependent upon the kidney preserved with the perfusate.

Reperfusion was immediate without any signs of vasospasm or reperfusion injury. At no time was hypothermia introduced during the period of reimplantation which entailed a period of warm ischemia of approximately 30 minutes. As shown in FIG. 2, twenty-four hours posttransplant, normal renal function was demonstrated (test dogs #3 and #4).

In both the auto- and the allotransplant models, the in situ preservation using the perfusate of the present invention at elevated temperatures (37° C.) resulted in normal serum chemistries (serum creatinine <2.0 mg/dL) within 24 hours of transplantation.

A control experiment consisted of an animal experiencing two hours of warm ischemia caused by clamping of the aorta and vena cava without perfusion with the perfusate solution of the present invention. In this animal, as illustrated in FIG. 2, the serum creatinine level was elevated at 24 hours posttreatment. The serum creatinine level continued to rise and the animal was euthanized on post transplant day 3 with a final serum creatinine level of 8.5 mg/dl.

At the time of sacrifice all kidneys were evaluated blindly for histology. In all cases, the kidneys preserved in situ with the perfusate of the present invention appeared to be normal.

Conclusion

The results from these studies demonstrate the significance of the technology of the present invention. The histological studies indicate that with current technology, using VIASPAN and optimized cold preservation techniques, dilation of the tubules was detected along with edema. Therefore, even optimized cold preservation leads to tubule damage. In contrast, the warm preservation model using the preservation solution of the present invention supported normal glomerular and tubule histology, with no dilation or edema at the same time period of preservation. These findings alone support the significance of the warm preservation technology. Further, the preservation solution of the present invention is useful for in situ preservation, and is superior to state-of-the-art perfusates for the preservation of organs ex vivo at a temperature of 25° C.

In vitro studies have demonstrated that organs can be preserved in the preservation solution at physiologic temperatures ranging from 25° C.–37° C. for up to 18 hours, and demonstrate stable flow rates, pressures, oxygen consumption, diuresis, and glucose consumption.

Most importantly, organs preserved at warm temperatures, 25° C. or 37° C., with the perfusate of this invention, demonstrated normal functional capacity (serum creatinine <2.0 mg/dL) 24 hours after transplantation. The perfusate of the present invention therefore supports optimized organ preservation without concomitant severe hypothermia, and provides for the opportunity to substantially expand the existing organ donor pool.

EXAMPLE 7

The Role of PFOB Supplementation

To further determine the efficacy of the preservation solution of the present invention in preserving organs using warm organ preservation technology, two canine renal autotransplantations were performed. The first evaluated the role of the liquid fluorocarbon emulsion in saline. The second evaluated the role of the basal cell culture medium alone.

In each dog, the left kidney was nephrectomized for the preservation studies. The intrinsic kidney maintained the dog during the period of ex vivo preservation. Just prior to reimplantation, the intrinsic kidney was nephrectomized. The preserved kidney was reimplanted in the capsule of the intrinsic kidney which had just been nephrectomized. At no time were hypothermic conditions employed, not even during the vascular reconstruction.

Results a. Perfluorocarbon in saline

The kidney was flushed with a solution consisting of 20% v/v of 90% PFOB emulsion in a saline solution. The renal artery was cannulated and the kidney was placed on a MOX-100 unit for organ preservation at 32° C. for five hours. The kidney developed a patchy appearance during the flushing, but flushed well. The kidney demonstrated poor flow dynamics within a few minutes of being placed on the preservation system. Visible swelling developed within the first thirty minutes of preservation, along with discoloration of the lobes. The flow dynamics continued to deteriorate during the preservation period, with periods of pronounced elevations in pressures. By two hours, the kidneys demonstrated pronounced swelling with pressures in excess of 140 mmHg. At four hours, the kidney was severely discolored, demonstrated virtually no vascular flow, and had begun to leak around the cannula. At five hours of preservation, the perfusion was discontinued. The kidney was discolored, edematous, more then twice its original size, and demonstrated no flow. The unacceptable flow dynamics lead to a decision not to transplant.

The kidney was evaluated histologically. The glomerular capillaries and the blood vessels were found to be dilated.

While the tubules were not necrosed, substantial interstitial edema was found.

b. Basal Perfusate Alone

The kidney was flushed with a solution consisting of the basal solution described in Formula 1 of Table I alone (no PFOB supplementation). The kidney flushed well, 500 cc in less than eight minutes. The renal artery was cannulated and the kidney was placed on a MOX-100 unit for organ preservation at 32° C. for five hours. The kidney perfused well throughout the period of preservation without alterations in pressure or flow. At three hours the kidney developed a splotchy appearance with areas of whitish discoloration, which may have been caused by leaky capillaries. After five hours of preservation, the kidney was autotransplanted. Anastomosis time was prolonged, more than 45 minutes. The kidney reperfused well, exhibiting good turgor. The kidney produced urine almost immediately after the circulation was restored. The dog voided 30 minutes after transplantation, and again at 3 hours post-transplantation. The dog developed bloody urine the next morning and had a serum creatinine level of 4.7 mg/dl.

Upon histologic evaluation, the kidney demonstrated autolysis and a band of interstitial infiltration of polymorphonuclear cells. These results were suggestive of reperfusion injury, secondary to the prolonged period of anoxia during the vascular reconstruction.

Neither the PFOB emulsion in saline nor the basal perfusate without PFOB can provide adequate preservation for an organ at elevated temperatures. PFOB emulsion in saline resulted in such poor perfusion that the kidney could not be transplanted. The basal perfusate alone provides acceptable preservation in terms of the in vitro criteria evaluated, however, upon transplantation, the kidney suffered reperfusion injury. The reperfusion injury may be secondary to the anoxia during the reanastomosis which can range from 20 to 45 minutes. Preservation of the kidney using the perfluorocarbon supplemented preservation solution totally eliminates this injury.

Therefore, the perfusate of this invention comprises a basal medium comprising a supplemented mammalian tissue culture media which is capable of supporting normal endothelial and tubule function. Supplementation with fluorocarbon emulsion provides adequate oxygen delivery which supports the ongoing metabolism of the organ. The perfusate of this invention provides optimized organ preservation at elevated temperatures and results in the normal and immediate function of the organ upon transplantation.

It should be understood that the embodiments and examples of the present invention, as described herein, are for purposes of illustration only, and not limitation.

What is claimed is:

1. A method for preserving an organ prior to transplantation, comprising the steps of:

flushing an organ with a preservation solution comprising one or more serum proteins, retinal-derived growth factor in a range of about 0.001–5 g/L, one or more mucopolysaccharides, cyclodextrin, and emulsified liquid fluorocarbon, wherein said fluorocarbon comprises between about 1% and 50% v/v of said preservation solution; and thereafter storing said organ at a temperature between about 18° C. and about 37° C, for at least 15 minutes.

2. The method of claim 1, wherein said flushing step is performed in situ.

3. The method of claim 1, wherein said flushing step is performed ex vivo.

4. The method of claim 1, wherein said flushing step and said storing step are performed while said organ remains in situ.

5. The method of claim 1, wherein said flushing step and said storing step are performed while said organ remains ex vivo.

6. A preservation solution which supports the preservation of organs without hypothermia, comprising:
one or more serum proteins, retinal-derived growth factor in a range of about 0.001–5 g/L, one or more mucopolysaccharides, cyclodextrin, and emulsified liquid fluorocarbon, wherein said fluorocarbon comprises between about 1% and 50% v/v of said preservation solution.

7. The preservation solution of claim 6, further comprising magnesium, amino acids, glucose, polysaccharide and salts.

8. The preservation solution of claim 6, wherein said serum protein is selected from the group consisting of transferrin, insulin and albumin.

9. The preservation solution of claim 6, wherein said mucopolysaccharide is selected from the group consisting of heparin and chondroitin sulfate.

10. The preservation solution of claim 6, wherein said fluorocarbon is perfluorooctylbromide.

11. The preservation solution of claim 6, wherein said preservation solution comprises a solution having an osmolarity of from about 330 to about 600 mOsM.

12. The preservation solution of claim 6, wherein said preservation solution comprises a solution having an osmolarity of from about 340 to about 450 mOsM.

13. The preservation solution of claim 6, wherein said fluorocarbon comprises between about 5% to about 40% v/v of said preservation solution.

14. The preservation solution of claim 6, wherein said fluorocarbon comprises between about 15% to about 25% v/v of said preservation solution.

15. The preservation solution of claim 6, wherein said fluorocarbon emulsion has a particle size of less than about 0.5 microns.

16. A method for organ transplantation, comprising the steps of:
identifying an organ to be transplanted;
flushing said organ with a preservation solution comprising one or more serum proteins, retinal-derived growth factor in a range of about 0.001–5 g/L, one or more mucopolysaccharides, cyclodextrin, and emulsified liquid fluorocarbon, wherein said fluorocarbon comprises between about 1% and 50% v/v of said preservation solution;
continuously perfusing said organ with said preservation solution at a temperature between about 18° C. and about 37° C. for at least 15 minutes; and thereafter
transplanting said organ into a recipient.

17. The method of claim 16, wherein said flushing step is performed in situ.

18. The method of claim 16, wherein said flushing step is performed ex vivo.

19. The method of claim 16, wherein said flushing step and said perfusing step are performed while said organ remains in situ.

20. The method of claim 16, wherein said flushing step and said perfusing step are performed while said organ remains ex vivo.

21. The method of claim 16, wherein said preservation solution further comprises magnesium, amino acids, glucose, polysaccharide and salts.

22. The method of claim 16, wherein said preservation solution comprises a solution having an osmolarity of from about 330 to about 600 mOsM.

23. The method of claim 16, wherein said preservation solution comprises a solution having an osmolarity of from about 340 to about 450 mOsM.

24. The method of claim 16, wherein said fluorocarbon comprises between about 5% to about 40% v/v of said preservation solution.

25. The method of claim 16, wherein said fluorocarbon comprises between about 15% to about 25% v/v of said preservation solution.

\* \* \* \* \*